United States Patent
Martos et al.

(10) Patent No.: US 9,422,273 B2
(45) Date of Patent: *Aug. 23, 2016

(54) COMPOUNDS ACT AT MULTIPLE PROSTAGLANDIN RECEPTORS GIVING A GENERAL ANTI-INFLAMMATORY RESPONSE

(71) Applicant: Allergan, Inc., Irvine, CA (US)

(72) Inventors: Jose L. Martos, Basildon Essex (GB); William R. Carling, Bishop's Stortford (GB); David F. Woodward, Lake Forest, CA (US); Jenny W. Wang, Irvine, CA (US); Jussi J. Kangasmetsa, Essex (GB)

(73) Assignee: ALLERGAN, INC., Irvine, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/792,406

(22) Filed: Jul. 6, 2015

(65) Prior Publication Data

US 2016/0068520 A1 Mar. 10, 2016

Related U.S. Application Data

(63) Continuation of application No. 14/178,982, filed on Feb. 12, 2014, now Pat. No. 9,085,567, which is a continuation of application No. 13/817,949, filed as application No. PCT/US2011/048361 on Aug. 19, 2011, now Pat. No. 8,653,118.

(60) Provisional application No. 61/375,406, filed on Aug. 20, 2010.

(51) Int. Cl.
| | | |
|---|---|---|
| *C07D 413/04* | (2006.01) | |
| *A61K 31/422* | (2006.01) | |
| *C07D 413/14* | (2006.01) | |
| *C07C 65/30* | (2006.01) | |
| *C07C 237/06* | (2006.01) | |
| *C07C 271/20* | (2006.01) | |
| *C07C 309/67* | (2006.01) | |
| *C07D 207/16* | (2006.01) | |
| *C07D 317/46* | (2006.01) | |

(52) U.S. Cl.
CPC ............ *C07D 413/04* (2013.01); *C07C 65/30* (2013.01); *C07C 237/06* (2013.01); *C07C 271/20* (2013.01); *C07C 309/67* (2013.01); *C07D 207/16* (2013.01); *C07D 317/46* (2013.01); *C07D 413/14* (2013.01)

(58) Field of Classification Search
None
See application file for complete search history.

(56) References Cited

U.S. PATENT DOCUMENTS

| 4,166,452 A | 9/1979 | Generales |
| 4,256,108 A | 3/1981 | Theeuwes |
| 4,265,874 A | 5/1981 | Bonsen |
| 5,280,034 A | 1/1994 | Hall |
| 6,511,999 B2 | 1/2003 | Burk |
| 8,653,118 B2 | 2/2014 | Martos |
| 9,085,567 B2 | 7/2015 | Martos |
| 2004/0162323 A1 | 8/2004 | Krauss |
| 2005/0054699 A1 | 3/2005 | Krauss |
| 2005/0065200 A1 | 3/2005 | Woodward |

FOREIGN PATENT DOCUMENTS

| JP | 2003508396 | 3/2003 |
| WO | 97-03973 | 2/1997 |
| WO | 01-16132 | 3/2001 |

OTHER PUBLICATIONS

Hall, Steven et al, Synthesis of Pyrrolidine Oxazoles as Thromboxane A2/Endoperoxide Receptor Antagonists, Bioorganic & Medicinal Chemistry Letters, 1993, 1263-1266, 3(6).
Remingtons, Remingtons_16th, Pharmaceutical Sciences, 1980, 1-10, 16, Remingtons_16th.
Notification of the International Search Report and Written Opinion mailed on Sep. 29, 2011 for PCT/US2011/048361 filed on Aug. 19, 2011 in the name of Allergan, Inc.

*Primary Examiner* — Alicia L Otton
(74) *Attorney, Agent, or Firm* — Jonathan Bass (57) ABSTRACT

The present invention provides compounds, that are N-alkyl-2-(1-(5-substituted-2-(3-oxo-3-(trifluoromethylsulfonamido)propyl)benzyl)pyrrolidin-2-yl)oxazole-4-carboxamide wherein the 5 substituent is selected from the group consisting of halo and alkyloxy radicals. The compound may be represented by the following formula

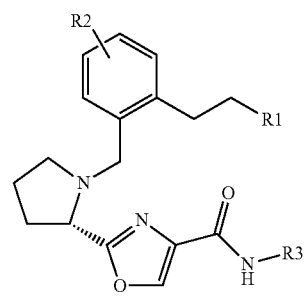

wherein $R_1$ is selected from the group consisting of $CO_2R_7$ and $CON(R_7)SO_2R_7$ wherein $R_1$, $R_2$, $R_3$, $R_4$, and $R_7$ are as defined in the specification. The compounds may be administered to treat $DP_1$, FP, $EP_1$, $EP_3$, TP and/or $EP_4$ receptor mediated diseases or conditions.

7 Claims, 2 Drawing Sheets

FIGURE 1

Scheme 1

FIGURE 2

Scheme 2

COMPOUNDS ACT AT MULTIPLE PROSTAGLANDIN RECEPTORS GIVING A GENERAL ANTI-INFLAMMATORY RESPONSE

CROSS REFERENCE TO RELATED APPLICATIONS

This application is a continuation of U.S. application Ser. No. 14/178,982 filed Feb. 12, 2014, which is a continuation of U.S. application Ser. No. 13/817,949 filed Feb. 20, 2013, which is a national stage application under 35 U.S.C. §371 of PCT Patent Application No. PCT/US11/48361 filed Aug. 19, 2011 which claims the benefit of U.S. Provisional Patent Application Ser. No. 61/375,406, filed Aug. 20, 2010, each of which are incorporated herein by reference in their entirety.

BACKGROUND OF THE INVENTION

1. Field of the Invention

This invention relates to compounds, to processes for their preparation, to pharmaceutical compositions containing them and to their use in medicine, in particular their use in the treatment of conditions mediated by the action of ligands for the $DP_1$, FP, TP, $EP_1$ $EP_3$ and $EP_4$ prostaglandin (PG) receptors. The present compounds have the general structure shown below and act at different prostaglandin receptors to thereby provide a general anti-inflammatory response.

2. Background of the Related Art

The $EP_1$ receptor is a 7-transmembrane receptor and its natural ligand is the prostaglandin $PGE_2$. $PGE_2$ also has affinity for the other EP receptors (types $EP_2$, $EP_3$ and $EP_4$). The $EP_1$ receptor is associated with smooth muscle contraction, pain (in particular inflammatory, neuropathic and visceral), inflammation, allergic activities, renal regulation and gastric or enteric mucus secretion.

Prostaglandin $E_2$ ($PGE_2$) exerts allodynia through the $EP_1$ receptor subtype and hyperalgesia through $EP_2$ and $EP_3$ receptors in the mouse spinal cord. Furthermore, it has been shown that in the $EP_1$ knockout mouse pain-sensitivity responses are reduced by approximately 50%. $EP_1$ receptor antagonist (ONO-8711) reduces hyperalgesia and allodynia in a rat model of chronic constriction injury and inhibits mechanical hyperalgesia in a rodent model of post-operative pain. The efficacy of $EP_1$ receptor antagonists in the treatment of visceral pain in a human model of hypersensitivity has been demonstrated. Thus, selective prostaglandin ligands, agonists or antagonists, depending on which prostaglandin E receptor subtype is being considered, have anti-inflammatory, antipyretic and analgesic properties similar to a conventional non-steroidal anti-inflammatory drug, and in addition, inhibit hormone-induced uterine contractions and have anti-cancer effects. These compounds have a diminished ability to induce some of the mechanism-based side effects of NSAIDs, which are indiscriminate cyclooxygenase inhibitors. In particular, the compounds have a reduced potential for cardiovascular toxicity, a reduced effect on bleeding times and a lessened ability to induce asthma attacks in aspirin-sensitive asthmatic subjects. Moreover, as a result of sparing potentially beneficial prostaglandin pathways, these agents may have enhanced efficacy over NSAIDS and/or COX-2 inhibitors. (See Pub. No. US 2005/0065200 for other diseases that may be treated by EP4 receptor antagonists which is hereby incorporated by reference in its entirety.)

$EP_3$ receptors have been implicated in pain and hyperalgesia and hypepyrexia. Thus, $EP_3$ antagonists may be useful for treating pain, inflammation and fever. Additional uses include treatment of pre-term labor, over-active bladder disorders, cancer and cardiovascular disease.

The TP (also known as $TxA_2$) receptor is a prostanoid receptor subtype stimulated by the endogenous mediator thromboxane. Activation of this receptor results in various physiological actions primarily incurred by its platelet aggregatory and smooth muscle constricting effects, thus opposing those of prostacyclin receptor activation.

TP receptors have been identified in human kidneys in the glomerulus and extraglomerular vascular tissue. Activation of TP receptors constricts glomerular capillaries and suppresses glomerular filtration rates indicating that TP receptor antagonists could be useful for renal dysfunction in glomerulonephritis, diabetes mellitus and sepsis.

Activation of TP receptors induces bronchoconstriction, an increase in microvascular permeability, formation of mucosal edema and mucus secretion, which are typical characteristic features of bronchial asthma. TP antagonists have been investigated as potential asthma treatments resulting in, for example, orally active Seratrodast (AA-2414). Ramatroban is another TP receptor antagonist currently undergoing phase III clinical trials as an anti-asthmatic compound.

Since the $DP_1$ receptor may trigger an asthmatic response in certain individuals, compounds that have $DP_1$ antagonist properties may be useful as anti-asthmatic drugs. (See Pub. No. 2004/0162323 for the disclosure of other diseases and conditions that may be treated with DP antagonists.) Finally, the FP receptor modulates intraocular pressure and mediates smooth muscle contraction of the sphincter muscles in the gastrointestinal tract and the uterus. Thus, antagonists of the FP receptor are useful for treating reproductive disorders. (See U.S. Pat. No. 6,511,999 for other diseases and conditions that may be treated with FP receptor antagonists.)

SUMMARY OF THE INVENTION

This invention provides compounds, that are N-alkyl-2-(1-(2-(3-oxo-3-(trifluoromethylsulfonamido)propyl)benzyl) pyrrolidin-2-yl)oxazole-4-carboxamides, e.g. N-alkyl-2-(1-(5-substituted-2-(3-oxo-3-(trifluoromethylsulfonamido) propyl)benzyl)pyrrolidin-2-yl)oxazole-4-carboxamides wherein the 5 substituent is selected from the group consisting of halo and alkyloxy radicals.

Some embodiments of the invention are described in the following paragraphs:

1. A compound, that is a N-alkyl-2-(1-(5-substituted-2-(3-oxo-3-(trifluoromethylsulfonamido)propyl)benzyl)pyrrolidin-2-yl)oxazole-4-carboxamide wherein the 5 substituent is selected from the group consisting of halo and alkyloxy radicals.

2. The compound of paragraph 1 wherein said alkyl radical is a n-alkyl radical.

3. The compound of paragraph 2 wherein said n-alkyl radical comprises from 5 to 10 carbon atoms.

4. The compound of paragraphs 1-3 wherein said n-alkyl radical is octyl.

5. The compound of paragraphs 1-2 wherein said alkyl radical is a cycloalkyl radical.

6. The compound of paragraph 5 wherein said cycloalkyl radical is a cyclohexyl-n-alkyl radical.

7. The compound of paragraphs 5-6 wherein said cyclohexyl-n-alkyl radical is cyclohexylbutyl.

8. The compound of paragraph 1 wherein the 5-substituent is selected from the group consisting of fluoro and chloro.

9. The compound of paragraph 1 wherein said alkyloxy is selected from the group consisting of methyloxy and dioxol.

10. A compound, that is selected from the group consisting of N-alkyl-2-(1-(5-substituted-2-(3-oxo-3-(trifluoromethylsulfonamido)propyl)benzyl)pyrrolidin-2-yl)oxazole-4-carboxamide, 3-(2-{2R-[4-(4-alkylcarbamoyl)-oxazol-2-yl]-pyrrolidin-1-ylmethyl}-4-substituted-phenyl)-propionic acid and alkyl esters thereof, wherein the substituent is selected from the group consisting of halo and alkyloxy radicals.

11. The compound of paragraphs 1-10 wherein said compound is selected from the group consisting of:
(S)—N-(4-cyclohexylbutyl)-2-(1-(5-fluoro-2-(3-oxo-3-(trifluoromethylsulfonamido)propyl)benzyl)pyrrolidin-2-yl)oxazole-4-carboxamide,
(S)—N-(4-cyclohexylbutyl)-2-(1-(5-methoxy-2-(3-oxo-3-(trifluoromethylsulfonamido)propyl)benzyl)pyrrolidin-2-yl)oxazole-4-carboxamide,
(S)—N-(4-cyclohexylbutyl)-2-(1-(5-chloro-2-(3-oxo-3-(trifluoromethylsulfonamido)propyl)benzyl)pyrrolidin-2-yl)oxazole-4-carboxamide,
N-(4-cyclohexylbutyl)-2-(1-{[6-(3-oxo{[(trifluoromethylsulfonamido)propyl)-1,3-benzodioxol-5-yl]methyl}pyrrolidin-2-yl)-1,3-oxazole-4-carboxamide and
2-{1-[5-fluoro-2-(3-oxo-3-{[(trifluoromethyl)sulfonyl]amino}propyl)benzyl]pyrrolidin-2-yl}-N-octyl-1,3-oxazole-4-carboxamide.

12. A compound having the following formula:

wherein $R_1$ is selected from the group consisting of $CO_2R_7$ and
$CON(R_7)SO_2R_7$ wherein $R_7$ is selected from the group consisting of H, alkyl and aryl, wherein said alkyl and aryl may be substituted with halo or haloalkyl,
$R_2$ is selected from the group consisting of H, alkyl, halogen, $OR_7$ and $OC(R_7)_2O$; and
$R_3$ is selected from the group consisting of H and alkyl; provided however, when $R_1$ is $CO_2R_7$, $R_2$ is not H.

13. The compound of paragraph 12 wherein $R_2$ is selected from the group consisting of F, Cl, $OCH_3$ and $O(CH_2)O$.

14. The compound of paragraph 12 wherein $R_3$ is alkyl.

15. The compound of paragraphs 12-13 wherein, $R_3$ is $(CH_2)_nCH_2R_2$, wherein n is an integer of from 4 to 9 and $R_7$ is H or cyclohexyl.

16. The compound of paragraph 12 wherein, $R_7$ is selected from the group consisting of methyl, ethyl, i-propyl, trifluoromethyl and cyclopropyl.

17. The compound of paragraph 12 wherein, $R_1$ is $NHSO_2R_7$.

18. The compound of paragraph 17 wherein, $R_7$ is selected from the group consisting of methyl, ethyl, i-propyl, trifluoromethyl and cyclopropyl.

19. The compound of paragraphs 12 and 17 wherein $R_2$ is selected from the group consisting of F, Cl, $OCH_3$ and $O(CH_2)O$.

20. The compound of paragraphs 12 and 17 wherein, $R_3$ is $(CH_2)_nCH_2R_2$, wherein n is an integer of from 4 to 9 and $R_7$ is H or cyclohexyl 21. A method of making an N-alkyl-2-(1-(5-substituted-2-(3-oxo-3-(trifluoromethylsulfonamido)propyl)benzyl)pyrrolidin-2-yl)oxazole-4-carboxamide which comprises reacting the corresponding 3-(2-{2R-[4-(4-alkylcarbamoyl)-oxazol-2-yl]-pyrrolidin-1-ylmethyl}-4-substituted-phenyl)-propionic acid with cyanuric acid and trifluoromethanesulfonamide to yield said N-alkyl-2-(1-(5-substituted-2-(3-oxo-3-(trifluoromethylsulfonamido)propyl)benzyl)pyrrolidin-2-yl)oxazole-4-carboxamide.

22. The method of paragraph 21 wherein said 3-(2-{2R-[4-(4-alkylcarbamoyl)-oxazol-2-yl]-pyrrolidin-1-ylmethyl}-4-substituted-phenyl)-propionic acid is made by hydrolyzing the corresponding propionic alkyl ester, i.e. 3-(2-{2R-[4-(4-Alkylcarbamoyl)-oxazol-2-yl]-pyrrolidin-1-ylmethyl}-4-substituted-phenyl)-propionic acid alkyl ester to yield said 3-(2-{2R-[4-(4-Alkylcarbamoyl)-oxazol-2-yl]-pyrrolidin-1-ylmethyl}-4-substituted-phenyl)-propionic acid.

23. The method of paragraph 22 wherein said 3-(2-{2R-[4-(4-alkylcarbamoyl)-oxazol-2-yl]-pyrrolidin-1-ylmethyl}-4-substituted-phenyl)-propionic acid alkyl ester is made by reacting the corresponding aldehyde and proline, i.e. 2R-Pyrrolidin-2-yl-oxazole-4-carboxylic acid alkylamide is reacted with 3-(4-substituted-2-formyl-phenyl)-propionic acid alkyl ester to yield said 3-(2-{2R-[4-(4-alkylcarbamoyl)-oxazol-2-yl]-pyrrolidin-1-ylmethyl}-4-substituted-phenyl)-propionic acid alkyl ester.

24. A method according to any of paragraphs 21, 22 or 23 wherein the phenyl substituent is selected from the group consisting of fluoro, chloro, methoxy and dioxol.

25. A method according to any of paragraphs 21, 22 or 23 wherein said N-alkyl is selected from the group consisting of octyl and cyclohexylbutyl.

26. A method according to any of paragraphs 21, 22 or 23 wherein said propionic acid alkyl ester is propionic acid methyl ester.

27. A method according to paragraph 26 wherein said 3-(2-{2R-[4-(4-alkylcarbamoyl)-oxazol-2-yl]-pyrrolidin-1-ylmethyl}-4-substituted-phenyl)-propionic acid is reacted with cyanuric acid in the presence of pyridine at reflux, the resulting reaction mixture cooled to room temperature, diluted with ethyl acetate and water to separate a crude organic product and said crude organic product is dissolved in $CH_2Cl_2$ and DMAP, trifluromethanesulfonamide is added and the resulting mixture is stirred at room temperature under nitrogen to yield said N-alkyl-2-(1-(5-substituted-2-(3-oxo-3-(trifluoromethylsulfonamido)propyl)benzyl)pyrrolidin-2-yl)oxazole-4-carboxamide.

28. A method comprising administering a compound having the following formula:

wherein $R_1$ is selected from the group consisting of $CO_2R_7$ and
$CON(R_7)SO_2R_7$ wherein $R_7$ is selected from the group consisting of H, alkyl and aryl, wherein said alkyl and aryl may be substituted with halo or haloalkyl
$R_2$ is selected from the group consisting of H, alkyl, halogen, $OR_7$ and $OC(R_7)_2O$; and
$R_3$ is selected from the group consisting of H and alkyl; provided however, when $R_1$ is $CO_2R_7$, $R_2$ is not H.
29 The method of paragraph 28 wherein said compound is administered to treat $DP_1$, FP, $EP_1$, $EP_3$, TP and/or $EP_4$ receptor mediated diseases or conditions.
30. A method comprising administering a compound to treat $DP_1$, FP, $EP_1$, $EP_3$, TP and/or $EP_4$ receptor mediated diseases or conditions wherein said compound has the following formula:

wherein $R_1$ is selected from the group consisting of $CO_2R_7$ and
$CON(R_7)SO_2R_7$ wherein $R_7$ is selected from the group consisting of H, alkyl and aryl, wherein said alkyl and aryl may be substituted with halo or haloalkyl
$R_2$ is selected from the group consisting of H, alkyl, halogen, $OR_7$ and $OC(R_7)_2O$; and
$R_3$ is selected from the group consisting of H and alkyl.

DETAILED DESCRIPTION OF THE INVENTION

The following terms are used to define the disclosed invention.

"Alkyl" refers to a straight-chain, branched or cyclic saturated aliphatic hydrocarbon. Preferably, the alkyl group has 1 to 12 carbons. More preferably, it is an alkyl of from 4 to 10 carbons, most preferably 4 to 8 carbons. Typical alkyl groups include methyl, ethyl, propyl, isopropyl, butyl, isobutyl, tertiary butyl, pentyl, hexyl and the like. The alkyl group may be optionally substituted with one or more substituents are selected from the group consisting of hydroxyl, cyano, alkoxy, $=O$, $=S$, $NO_2$, halogen, dimethyl amino, and SH.

"Cycloalkyl" refers to a cyclic saturated aliphatic hydrocarbon group. Preferably, the cycloalkyl group has 3 to 12 carbons. More preferably, it has from 4 to 7 carbons, most preferably 5 or 6 carbons.

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of alkyl, hydroxyl, halogen, $COOR^6$, $NO_2$, $CF_3$, $N(R^6)_2$, $CON(R^6)_2$, $SR^6$, sulfoxy, sulfone, CN and $OR^6$, wherein $R^6$ is alkyl.

"Carbocyclic aryl" refers to an aryl group wherein the ring atoms are carbon.

"Heteroaryl" refers to an aryl group having from 1 to 3 heteroatoms as ring atoms, the remainder of the ring atoms being carbon. Heteroatoms include oxygen, sulfur, and nitrogen. Thus, heterocyclic aryl groups include furanyl, thienyl, pyridyl, pyrrolyl, N-lower alkyl pyrrolo, pyrimidyl, pyrazinyl, imidazolyl and the like. Preferably, the heteroaryl group has from 2 to 10 carbons. More preferably, it has from 3 to 10 carbons, most preferably 3 carbons.

The invention further relates to pharmaceutical compositions containing the above compounds in combination with a pharmaceutically-acceptable excipient and to their use in medicine, in particular their use in the treatment of conditions mediated by the action of ligands for the $DP_1$, FP, $EP_1$, $EP_3$ and $EP_4$ prostaglandin (PG) receptors. The compounds of this invention are also useful for treating conditions mediated by the action of ligands for the thromboxane (TP) receptor.

The present invention provides compounds having the general formula:

wherein R₁ is selected from the group consisting of $CO_2R_7$ and
$CON(R_7)SO_2R_7$ wherein $R_7$ is selected from the group consisting of H, alkyl and aryl, wherein said alkyl and aryl may be substituted with halo or haloalkyl, e.g. fluoro or fluoroalkyl;
$R_2$ is selected from the group consisting of H, alkyl, halogen, $OR_7$ and $OC(R_7)_2O$;
$R_3$ is selected from the group consisting of H and alkyl; provided however, when $R_1$ is $CO_2R_7$, $R_2$ is not H;
Preferably, $R_1$ is selected from the group consisting of $CO_2H$, $CO_2C_3H_7$ and $NHSO_2R_7$.
More preferably $R_1$ is $NHSO_2R_7$,
Preferably, $R_7$ is selected from the group consisting of methyl, ethyl, i-propyl, trifluoromethyl and cyclopropyl;
Preferably, $R_2$ is selected from the group consisting of F, Cl, $CH_3O$, $OCH_2O$ and H; and,
Preferably, $R_3$ is $(CH_2)_nCH_2R_7$, wherein n is an integer of from 4 to 9 and $R_7$ is H or cyclohexyl.
The most preferred compounds of the present invention are selected from the group consisting of:
(S)—N-(4-cyclohexylbutyl)-2-(1-(5-fluoro-2-(3-oxo-3-(trifluoromethylsulfonamido)propyl)benzyl)pyrrolidin-2-yl)oxazole-4-carboxamide;
(S)—N-(4-cyclohexylbutyl)-2-(1-(5-methoxy-2-(3-oxo-3-(trifluoromethylsulfonamido)propyl)benzyl)pyrrolidin-2-yl)oxazole-4-carboxamide;
(S)—N-(4-cyclohexylbutyl)-2-(1-(5-chloro-2-(3-oxo-3-(trifluoromethylsulfonamido)propyl)benzyl)pyrrolidin-2-yl)oxazole-4-carboxamide;
N-(4-cyclohexylbutyl)-2-(1-{[6-(3-oxo{[(trifluoromethylsulfonamido)propyl)-1,3-benzodioxol-5-yl]methyl}pyrrolidin-2-yl)-1,3-oxazole-4-carboxamide; and,
2-{1-[5-fluoro-2-(3-oxo-3-{[(trifluoromethyl)sulfonyl]amino}propyl)benzyl]pyrrolidin-2-yl}-N-octyl-1,3-oxazole-4-carboxamide.

Figure 1:
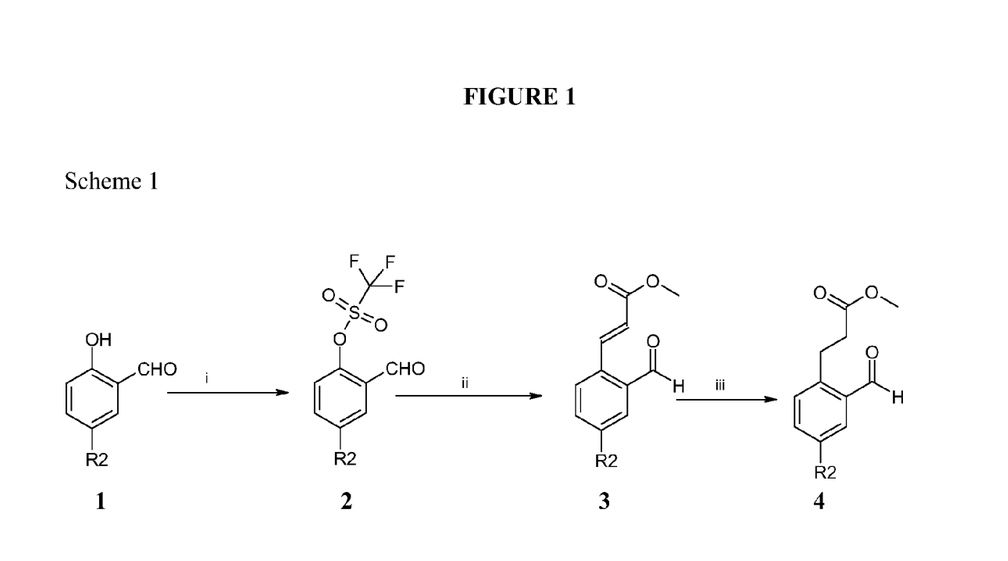
FIG. 1 shows the reaction scheme for the preparation of certain intermediate aldehyde compounds that are useful in preparing compounds of this invention; (Reagents: i) N-Phenylbis(trifluoromethanesulfinimide, Et3N, DMF; ii) methyl acrylate, Et3N, Pd(dppf)2Cl2; iii) H2, Palladium on Alumina, THF, MeOH); and, FIG. 2 shows the reaction scheme for the preparation of compounds of this invention from the reaction product of the aldehydes of FIG. 1 and a proline compound (Reagents: i) R3NH2, WSCDI, N-methylmorpholine, DMF; ii) H2, Palladium Hydroxide, THF, MeOH; iii) Z-L-proline, HBTU, Nmethylmorpholine, DMF; iv) Deoxo-fluor, DCM; v) CuBr2, HMTA, DCM, DBU; vi) H2, Palladium Hydroxide, MeOH; vii) sodiumtriacetoxyborohydride, DCM; viii) LiOH, THF, H2O; ix) cyanuric fluoride, THF, Pyridine; x) CF3SO2NH2, DMAP, DCM).
Figure 2:
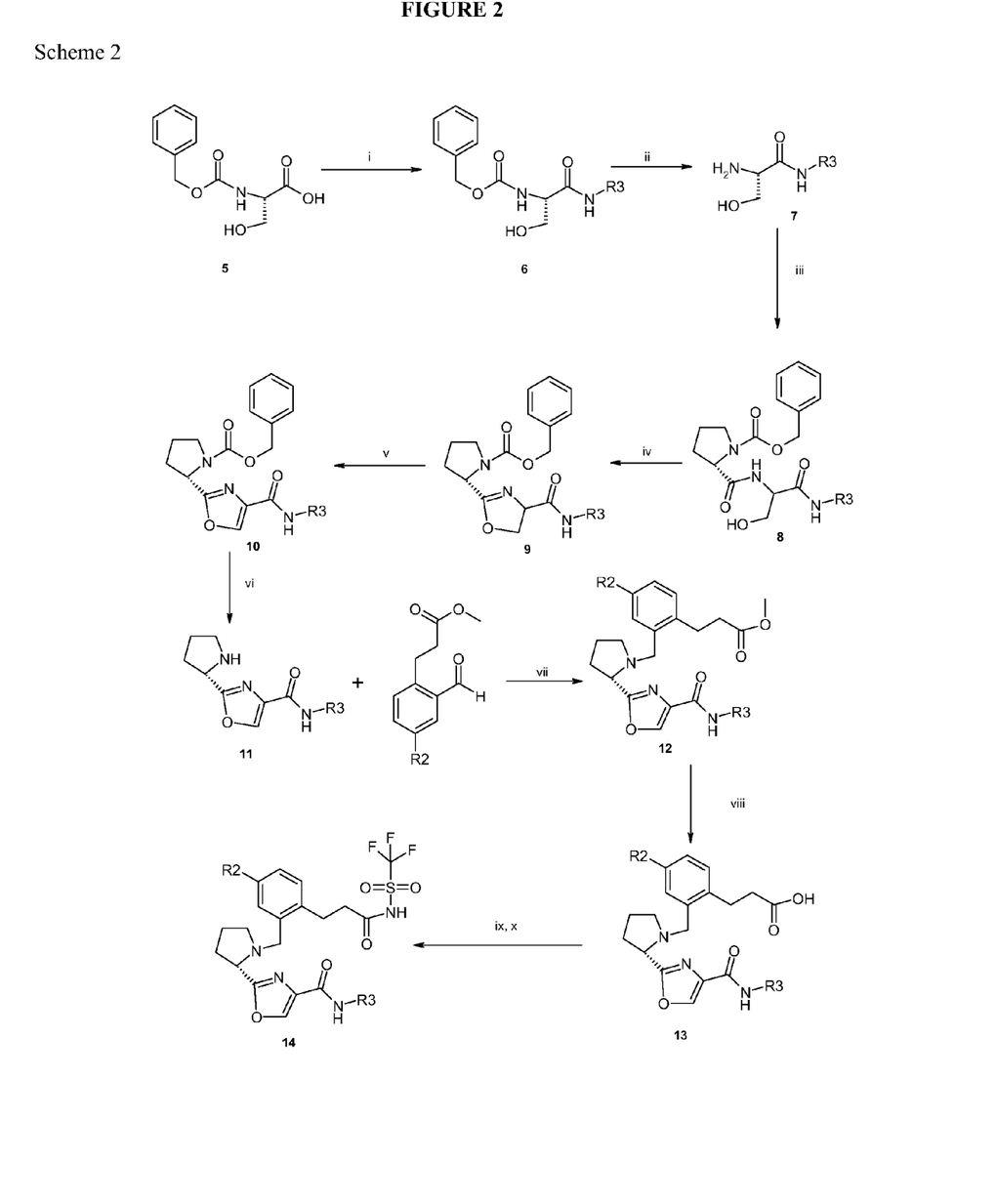

Certain of the compounds of the present invention may be prepared according to methods for preparing similar compounds—albeit compounds that are reported as thromboxane A 2 receptor antagonists or thromboxane A 2 synthetase inhibitors—as set forth in U.S. Pat. No. 5,280,034, which is hereby incorporated by reference. As shown in FIGS. 1 and 2, preferably, certain of the preferred compounds of the present invention are prepared by a method of making an N-alkyl-2-(1-(5-substituted-2-(3-oxo-3-(trifluoromethylsulfonamido)propyl)benzyl)pyrrolidin-2-yl)oxazole-4-carboxamide which comprises reacting the corresponding 3-(2-{2R-[4-(4-Alkylcarbamoyl)-oxazol-2-yl]-pyrrolidin-1-ylmethyl}-4-substituted-phenyl)-propionic acid with cyanuric acid and trifluoromethanesulfonamide to yield said N-alkyl-2-(1-(5-substituted-2-(3-oxo-3-(trifluoromethylsulfonamido)propyl)benzyl)pyrrolidin-2-yl)oxazole-4-carboxamide. In the above method, said 3-(2-{2R-[4-(4-alkylcarbamoyl)-oxazol-2-yl]-pyrrolidin-1-ylmethyl}-4-substituted-phenyl)-propionic acid may be reacted with cyanuric acid in the presence of pyridine, or other suitable base, at reflux, the resulting reaction mixture cooled to room temperature, diluted to separate out the organic product, preferably with ethyl acetate and water and said crude organic product is dissolved in $CH_2Cl_2$ and DMAP, trifluromethanesulfonamide is added and the resulting mixture is stirred at room temperature under nitrogen or other inert gas to yield said N-alkyl-2-(1-(5-substituted-2-(3-oxo-3-(trifluoromethylsulfonamido)propyl)benzyl)pyrrolidin-2-yl)oxazole-4-carboxamide.

Said 3-(2-{2R-[4-(4-alkylcarbamoyl)-oxazol-2-yl]-pyrrolidin-1-ylmethyl}-4-substituted-phenyl)-propionic acid may be made by hydrolyzing the corresponding propionic alkyl ester, i.e. 3-(2-{2R-[4-(4-Alkylcarbamoyl)-oxazol-2-yl]-pyrrolidin-1-ylmethyl}-4-substituted-phenyl)-propionic acid alkyl ester to yield said 3-(2-{2R-[4-(4-Alkylcarbamoyl)-oxazol-2-yl]-pyrrolidin-1-ylmethyl}-4-substituted-phenyl)-propionic acid.

Said 3-(2-{2R-[4-(4-alkylcarbamoyl)-oxazol-2-yl]-pyrrolidin-1-ylmethyl}-4-substituted-phenyl)-propionic acid alkyl ester is made by reacting the corresponding aldehyde and proline, i.e. 2R-Pyrrolidin-2-yl-oxazole-4-carboxylic acid alkylamide may be reacted with 3-(4-substituted-2-formyl-phenyl)-propionic acid alkyl ester to yield said 3-(2-{2R-[4-(4-alkylcarbamoyl)-oxazol-2-yl]-pyrrolidin-1-ylmethyl}-4-substituted-phenyl)-propionic acid alkyl ester.

Preferably, the phenyl substituent is selected from the group consisting of fluoro, chloro, methoxy and dioxol.

Preferably, said N-alkyl is selected from the group consisting of octyl and cyclohexylbutyl.

Preferably, said propionic acid alkyl ester is propionic acid methyl ester.

The reagents and conditions used in FIGS. 1 and 2 and the Examples may be abbreviated as follows:
Ac is acetyl or acetate;
DCM is dichloromethane;
TFA is trifluoroacetic acid;
DBU refers to 1,8-diazabicyclo[5.4.0]undec-7-ene;
DMF is dimethylformamide;
Me is methyl;
Et is ethyl;
THF is tetrahydrofuran;
DMAP is 4-dimethylaminopyridine;
HEPES (4-(2-hydroxyethyl)-1-piperazineethanesulfonic acid;
HMTA is hexamethylenetetramine; and,
HBTU is 2-(1H-benzotriazol-1-yl)-1,1,3,3-tetramethyluronium hexafluorophosphate.

The following examples are intended to illustrate the present invention.

Example 1

General Method 1

N-Phenylbis(trifluoromethanesulfinimide) (1.41 g, 3.94 mmol) was added portion-wise to a solution of the Phenol (3.57 mmol) and triethylamine (0.56 mL, 4 mmol) in DMF (3 mL) at room temperature and under nitrogen atmosphere. The resulting mixture was stirred overnight. The reaction was quenched with water (3 ml) and the mixture was extracted with diethyl ether (2×10 ml). The organic layer was dried (MgSO₄), filtered and the solvent was evaporated under vacuum. The crude compound was purified by column in a 20 g SPE cartridge using 20% $CH_2Cl_2$/80% iso-hexane as eluent to give the desired triflate as a black liquid (98%).

Example 1a

Trifluoro-methanesulfonic acid-4-fluoro-2-formyl-phenyl ester $^1$H-NMR (CDCl$_3$, 300 MHz): 10.26 (s, 1H, CHO), 7.69 (m, 1H, ArH), 7.45 (m, 2H, ArH). $^{19}$F-NMR(CDCl$_3$, 300 MHz) γ −73.1, −110

Example 1b

Trifluoro-methanesulfonic acid-4-Chloro-2-formyl $^1$H-NMR (CDCl$_3$, 300 MHz): 10.22 (s, 1H, CHO), 7.95 (d, 1H, J=2.6 Hz, ArH), 7.68 (dd, 1H, J=2.6, 8.6 Hz, ArH), 7.38 (d, 1H, J=8.6 Hz, ArH). $^{19}$F-NMR(CDCl$_3$, 300 MHz) −73.2

Example 1c

Trifluoro-methanesulfonic acid-4-methoxy-2-formyl $^1$H-NMR (CDCl$_3$, 300 MHz): 10.26 (s, 1H, CHO), 7.29 (m, 3H, ArH), 3.90 (s, 3H, —OCH$_3$). $^{19}$F-NMR(CDCl$_3$, 300 MHz) −73.2

Example 2

General Method 2

A mixture of the triflate (from General method 1) (3.37 mmol), methyl acrylate (0.70 ml), triethylamine (0.9 ml, 6.8 mmol) and Pd(dppf)$_2$Cl$_2$ (0.026 g) in THF (10 ml) was heated at reflux for 16 h under a nitrogen atmosphere. Water (10 ml) was added and the compound was extracted with ether (3×10 ml). The combined ether layers were washed with brine (10 ml), dried (MgSO4) and then evaporated to dryness under vacuum.

Then the crude compound was purified by column in a 25G Silica cartridge using 30% EtOAc/70% iso-hexane as eluent to give the conjugated ester as a light brown solid (41%).

Example 2a

(E)-3-(4-Fluoro-2-formyl-phenyl)-acrylic acid methyl ester $^1$H-NMR (CDCl$_3$, 300 MHz): 10.30 (s, 1H, CHO), 8.43 (d, 1H, J=15.9 Hz, —CH═CH—CO$_2$CH$_3$), 7.61 (m, 2H, ArH), 7.34 (m, 1H, ArH), 6.37 (d, 1H, J=15.9 Hz, —CH═CH—CO$_2$CH$_3$), 3.85 (s, 3H, —CO$_2$CH$_3$). $^{19}$F-NMR(CDCl$_3$, 300 MHz) δ −110

Example 2b

(E)-3-(4-Chloro-2-formyl-phenyl)-acrylic acid methyl ester

¹H-NMR (CDCl₃, 300 MHz): 10.25 (s, 1H, CHO), 8.41 (d, 1H, J=15.9 Hz, —CH=CH—CO₂CH₃), 7.84 (s, 1H, ArH), 7.88 (s, 2H, ArH), 6.37 (d, 1H, J=15.9 Hz, —CH=CH—CO₂CH₃), 3.82 (s, 3H, —CO₂CH₃).

Example 2c

(E)-3-(4-Methoxy-2-formyl-phenyl)-acrylic acid methyl ester

¹H-NMR (CDCl₃, 300 MHz): 10.35 (s, 1H, CHO), 8.47 (d, 1H, J=15.9 Hz, —CH=CH—CO₂CH₃), 7.61 (d, 1H, J=8.6 Hz, ArH), 7.39 (s, 1H, ArH), 7.16 (m, 1H, ArH), 6.33 (d, 1H, J=15.9 Hz, —CH=CH—CO₂CH₃), 3.91 (s, 3H, —OCH₃), 3.83 (s, 3H, —CO₂CH₃).

Example 2d (E)-3-(6-Formyl-benzo[1,3]dioxol-5-yl)-acrylic acid methyl ester

This derivative was prepared following general method 2 but starting from the commercially available aromatic bromide ¹H-NMR (CDCl₃, 300 MHz): 10.27 (s, 1H, CHO), 8.45 (d, 1H, J=15.9 Hz, —CH=CH—CO₂CH₃), 7.37 (s, 1H, ArH), 7.07 (s, 1H, ArH), 6.33 (d, 1H, J=15.9 Hz, —CH=CH—CO₂CH₃), 612 (s, 2H, —OCH₂O—), 3.85 (s, 3H, —CO₂CH₃).

Example 3

General Method 3

The unsaturated methyl ester (from General method 2) (0.3 mmol) was dissolved in a mixture of THF (2 mL) and MeOH (4 ml). Palladium on Alumina catalyst (35 mg) was added and the suspension was stirred for 1.5 h at room temperature under a hydrogen atmosphere. The catalyst was removed by filtration through Hyflo and the filtrate was evaporated under vacuum to give a yellow solid (70%).

Example 3a

3-(4-Fluoro-2-formyl-phenyl)-propionic acid methyl ester

¹H-NMR (CDCl₃, 300 MHz): 10.30 (s, 1H, CHO), 7.61 (m, 2H, ArH), 7.34 (m, 1H, ArH), 3.85 (s, 3H, —CO₂CH₃), 2.88 (m, 2H, ArCH₂CH₂CO₂Me), 2.63 (m, 2H, ArCH₂CH₂CO₂Me). ¹⁹F-NMR(CDCl₃, 300 MHz) δ −110

Example 3b

3-(4-Chloro-2-formyl-phenyl)-propionic acid methyl ester

¹H-NMR (CDCl₃, 300 MHz): 10.25 (s, 1H, CHO), 7.84 (s, 1H, ArH), 7.88 (s, 2H, ArH), 3.82 (s, 3H, —CO₂CH₃), 2.87 (m, 2H, ArCH₂CH₂CO₂Me), 2.59 (m, 2H, ArCH₂CH₂CO₂Me).

Example 3c

3-(4-Methoxy-2-formyl-phenyl)-propionic acid methyl ester

¹H-NMR (CDCl₃, 300 MHz): 10.35 (s, 1H, CHO), 7.61 (d, 1H, J=8.6 Hz, ArH), 7.39 (s, 1H, ArH), 7.16 (m, 1H, ArH), 3.91 (s, 3H, —OCH₃), 3.83 (s, 3H, —CO₂CH₃), 2.92 (m, 2H, ArCH₂CH₂CO₂Me), 2.61 (m, 2H, ArCH₂CH₂CO₂Me).

Example 3d

3-(6-Formyl-benzo[1,3]dioxol-5-yl)-propionic acid methyl ester

¹H-NMR (CDCl₃, 300 MHz): 10.27 (s, 1H, CHO), 7.37 (s, 1H, ArH), 7.07 (s, 1H, ArH), 612 (s, 2H, —OCH₂O—), 3.85 (s, 3H, —CO₂CH₃), 2.93 (m, 2H, ArCH₂CH₂CO₂Me), 2.63 (m, 2H, ArCH₂CH₂CO₂Me).

Example 4

General Method 4

A solution of Z-protected-L-Serine (5 g, 20.9 mmol), amine (25.1 mmol), WSC (6 g, 31.4 mmol), N-methylmorpholine (2.55 ml, 23 mmol) in DMF (150 ml) was stirred at room temperature for 16 h under a nitrogen atmosphere.

The reaction mixture was evaporated to dryness under vacuum and the residue was re-dissolved in EtOAc (100 ml). This solution was washed with 2M solution of HCl (2×75 mL), sat. Solution of sodium bicarbonate (2×75 mL), brine (2×75 mL) and dried (Na₂SO₄). The solvent was evaporated to give the Z-protected serine amide as a white solid (64%).

Example 4a

(2-Hydroxy-1-octylcarbamoyl)-ethyl)-carbamic-acid benzyl ester

¹H-NMR (CDCl₃, 300 MHz): 7.37 (m, 5H, ArH), 6.56 (m, 1H, NH), 5.83 (m, 1H, NH), 5.15 (s, 2H, ArCH₂—), 4.16 (m, 2H, CH₂OH), 3.67 (m, 1H, NHCHCO), 3.24 (m, 2H, CONHCH₂—), 1.49 (m, 2H, NHCH₂—CH₂—), 1.27 (m, 10H, —CH₂—CH₂—), 0.89 (m, 3H, —CH₃)

Example 5

General Method 5

The Z-protected serinamide (from General method 4) (0.98 mmol) was dissolved in a mixture of THF (25 ml) and MeOH (18 ml). Then Pd(OH)$_2$ (52 mg) was added and the reaction mixture was stirred for 16 h at room temperature under a hydrogen atmosphere. The palladium hydroxide was removed by filtration through Hyflo and the filtrate was evaporated under vacuum to give the free serine amide as a yellow solid (98%).

Example 5a

2-Amino-3-hydroxy-N-octyl-propionamide $^1$H-NMR (CDCl$_3$, 300 MHz): 3.84-3.73 (m, 2H, CH$_2$OH), 3.47 (m, 1H, NHCHCO), 3.26 (m, 2H, CONHCH$_2$—), 2.49 (bs, 2H, NH$_2$), 1.52 (m, 2H, NHCH$_2$—CH$_2$—), 1.29 (m, 10H, —CH$_2$—CH$_2$—), 0.89 (m, 3H, —CH$_3$)

Example 6

General Method 6

To a solution N-benzyloxicarbonyl-L-proline (14.86 mmol) and free serine amide (from General method 5) (16.35 mmol) in dimethylformamide (150 ml) under a nitrogen atmosphere, N-methylmorpholine (3.6 mL, 32.7 mmol) was added, followed by HBTU (6.2 g, 16.35 mmol). The resulting mixture was stirred at room temperature for 16 h.

After this time the solution was concentrated under vacuum and the residue was dissolved in ethyl acetate (100 mL). The solution was washed with 2M HCl solution (100 mL), a saturated solution of NaHCO$_3$ (100 mL) and dried over MgSO$_4$. Filtration and concentrated under vacuum yield the desired compound as a thick oil.

Example 6a

2R-(2-Hydroxy-1-octylcarbamoyl-ethylcarbamoyl)-pyrrolidine-1-carboxylic acid benzyl ester $^1$H-NMR (CDCl$_3$, 300 MHz): 7.35 (m, 5H, ArH), 5.15 (s, 2H, ArCH$_2$—), 4.48 (m, 1H, NCHCONH), 4.33 (m, 2H, CH$_2$OH), 4.07 (m, 1H, NHCHCO), 3.59 (m, 2H, CH$_2$NCO), 3.19 (m, 2H, CONHCH$_2$—), 2.20 (m, 2H, —CH$_2$—CH$_2$—), 1.94 (m, 2H, —CH$_2$—CH$_2$—), 1.49 (m, 2H, NHCH$_2$—CH$_2$—), 1.27 (m, 10H, —CH$_2$—CH$_2$—), 0.88 (m, 3H, —CH$_3$)

Example 7

General Method 7

To a solution of amide (from general method 6) (14.86 mmol) in dichloromethane (200 ml), at −25° C. under a nitrogen atmosphere, 40% solution of deoxo-fluor (17.09 mmol) was added and the resulting mixture was stirred at room temperature for 2.5 h.

After this time, a saturated solution of NaHCO$_3$ (200 mL) was added and the mixture was diluted with more CH$_2$Cl$_2$ (100 mL). The organic layer was separated, then washed with saturated brine (150 mL), and dried over MgSO$_4$. Filtration and concentrated in vacuo yielded the crude compound as a thick oil.

The residue was purified by column chromatography on silica using a solvent gradient starting from ethyl acetate/iso-hexane 1:1 to ethyl acetate/methanol 9:1, to isolate the title compound as a thick oil (72%).

Example 7a

2R-(4-Octylcarbamoyl-4,5-dihydro-oxazol-2-yl)-pyrrolidine-1-carboxylic acid benzyl ester $^1$H-NMR (CDCl$_3$, 300 MHz): 7.37 (m, 5H, ArH), 5.12 (s, 2H, ArCH$_2$—), 4.70-4.30 (m, 4H, NCHCONH+CH$_2$O—+NHCHCO), 3.55 (m, 2H, CH$_2$NCO), 3.22 (m, 2H, CONHCH$_2$—), 2.22 (m, 1H, —CH$_2$—CH$_2$—), 2.05 (m, 3H, —CH$_2$—CH$_2$—), 1.53 (m, 2H, NHCH$_2$—CH$_2$—), 1.26 (m, 10H, —CH$_2$—CH$_2$—), 0.88 (m, 3H, —CH$_3$)

Example 8

General Method 8

To a suspension of copper bromide (7.48 mmol) in degassed dichloromethane (21 mL), under nitrogen atmosphere and in a water bath, was added HMTA (7.48 mmol) followed by DBU (7.48 mmol) and the resulting mixture was stirred for 15 minutes. Then, a solution of oxazolidine (from general method 7) (1.87 mmol) in dichloromethane (11 ml) was added and the resulting mixture was stirred at room temperature for 16 h.

After this time, the solution was concentrated under vacuum and the residue was partitioned between ethyl acetate (30 mL) and a 1:1 sat. solution of NH$_4$Cl and NH$_3$ (30 mL). Then, the organic layer was separated and washed with Brine (30 mL), and dried over MgSO$_4$. Filtration and concentrated in vacuo yield the crude compound as a thick oil. The residue was purified by column chromatography on a 10 g silica SPE using ethyl acetate/iso-hexane 40%: 60% to isolate the title compound as a yellow solid (80%)

Example 8a

2R-(4-Octylcarbamoyl-oxazol-2-yl)-pyrrolidine-1-carboxylic acid benzyl ester $^1$H-NMR (CDCl$_3$, 300 MHz): 8.10 (s, 1H, =CH), 8.01 (s, 1H, =CH), 7.37 (m, 7H, ArH), 7.13 (m, 3H, ArH), 6.88-6.79 (m, 2H, NH), 5.21-4.95 (m, 8H, NCHCONH+PhCH$_2$O—+NHCHCO), 3.70 (m, 4H, CH$_2$NCO), 3.59 (m, 4H, CONHCH$_2$—), 2.30 (m, 2H, —CH$_2$—CH$_2$—), 2.06 (m, 6H, —CH$_2$—CH$_2$—), 1.61 (m, 4H, NHCH$_2$—CH$_2$—), 1.29 (m, 20H, —CH$_2$—CH$_2$—), 0.88 (m, 6H, —CH$_3$)

Example 9

General Method 9

The Z-protected oxazole (from general method 8) (0.98 mmol) was dissolved in MeOH (25 ml) then Pd(OH)$_2$ (52 mg) was added and the suspension was stirred overnight at room temperature under hydrogen. The palladium hydroxide was removed by filtration through Hyflo and the filtrate was evaporated under vacuum to give a yellow solid (95%).

Example 9a

2R-Pyrrolidin-2-yl-oxazole-4-carboxylic acid octylamide $^1$H-NMR (CDCl$_3$, 300 MHz): 8.15 (s, 1H, =CH), 7.03 (m, 1H, NH), 4.46 (m, 1H, NCH-Oxazole), 3.39 (dd, 2H, J=7, 14 Hz, CONHCH$_2$—), 3.24 (m, 2H, —CH$_2$N—), 2.30-1.88 (m, 4H, —CH$_2$—CH$_2$—), 1.59 (m, 2H, NHCH$_2$—CH$_2$—), 1.28 (m, 10H, —CH$_2$—CH$_2$—), 0.88 (m, 3H, —CH$_3$)

General Method 10

To a solution of aldehyde (from general method 3) (1.49 mmol) and free proline (from general method 9) (1.24 mmol) in CH₂Cl₂ (15 mL) was added sodium triacetoxyborohydride (0.369 g, 1.74 mmol). The mixture was stirred under a nitrogen atmosphere for 16 hours at room temperature.

The mixture was diluted with 15 mL of CH₂Cl₂ and water was added. The organic layer was separated, washed with saturated brine (30 mL), dried (Na₂SO₄) and the solvent was evaporated to give required product as a yellow solid (85%).

Example 10a

3-(2-{2R-[4-(4-Cyclohexyl-butylcarbamoyl)-oxazol-2-yl]-pyrrolidin-1-ylmethyl}-4-fluoro-phenyl)-propionic acid methyl ester ¹H-NMR (CDCl₃, 300 MHz): 8.13 (s, 1H, =CH), 7.55 (dd, 1H, J=5.5, 8.4 Hz, ArH), 7.17 (m, 1H, NH), 7.05 (dd, 1H, J=2.6, 9.5 Hz, ArH), 6.96 (dt, 1H, J=2.6, 8.4, ArH), 4.03 (d, 1H, J=11.9 Hz, —NCH₂Ar), 3.81 (s, 3H, —CO₂CH₃), 3.76 (t, 1H, J=7.7 Hz, NCH-Oxazole), 3.53 (d, 1H, J=11.9 Hz, —NCH₂Ar), 3.41 (dd, 2H, J=7, 14 Hz, CONHCH₂—), 3.10 (m, 2H, ArCH₂CH₂CO₂Me), 3.00 (m, 1H, —CH₂N—), 2.70 (m, 2H, ArCH₂CH₂CO₂Me), 2.40 (m, 1H, —CH₂N—), 2.69-1.85 (m, 4H, —CH₂—CH₂—), 1.71-1.55 (m, 9H, NHCH₂—CH₂—), 1.36 (m, 2H, —CH₂—CH₂—), 1.25-1.19 (m, 6H, —CH₂—CH₂—). ¹⁹F-NMR(CDCl₃, 300 MHz) δ –111

Example 10b

3-(2-{2R-[4-(4-Cyclohexyl-butylcarbamoyl)-oxazol-2-yl]-pyrrolidin-1-ylmethyl}-4-chloro-phenyl)-propionic acid methyl ester ¹H-NMR (CDCl₃, 300 MHz): 8.18 (d, 1H, J=15.9 Hz, —CH=CH—CO₂Me), 8.12 (s, 1H, =CH), 7.47 (m, 1H, ArH), 7.29 (m, 1H, ArH), 7.22 (m, 2H, ArH+NH), 6.31 (d, 1H, J=15.9 Hz, —CH=CH—CO₂Me), 3.97 (d, 1H, J=11.9 Hz, —NCH₂Ar), 3.80 (s, 3H, —CO₂CH₃), 3.73 (t, 1H, J=7.7 Hz, NCH-Oxazole), 3.52 (d, 1H, J=11.9 Hz, —NCH₂Ar), 3.40 (dd, 2H, J=7, 14 Hz, CONHCH₂—), 3.05 (m, 2H, ArCH₂CH₂CO₂Me), 2.99 (m, 1H, —CH₂N—), 2.71 (m, 2H, ArCH₂CH₂CO₂Me), 2.41 (m, 1H, —CH₂N—), 2.69-1.85 (m, 4H, —CH₂—CH₂—), 1.71-1.55 (m, 9H, NHCH₂—CH₂—), 1.36 (m, 2H, —CH₂—CH₂—), 1.25-1.19 (m, 6H, —CH₂—CH₂—).

Example 10c

3-(2-{2R-[4-(4-Cyclohexyl-butylcarbamoyl)-oxazol-2-yl]-pyrrolidin-1-ylmethyl}-4-methoxy-phenyl)-propionic acid methyl ester ¹H-NMR (CDCl₃, 300 MHz): 8.23 (d, 1H, J=15.9 Hz, —CH=CH—CO₂Me), 8.14 (s, 1H, =CH), 7.55 (d, 1H, J=8.4 Hz, ArH), 7.24 (m, 1H, NH), 6.82 (m, 2H, ArH), 6.27 (d, 1H, J=15.9 Hz, —CH=CH—CO₂Me), 4.02 (d, 1H, J=11.9 Hz, —NCH₂Ar), 3.82 (s, 3H, Ar—OCH₃), 3.80 (s, 3H, —CO₂CH₃), 3.72 (t, 1H, J=7.7 Hz, NCH-Oxazole), 3.50 (d, 1H, J=11.9 Hz, —NCH₂Ar), 3.41 (dd, 2H, J=7, 14 Hz, CONHCH₂—), 3.15 (m, 2H, ArCH₂CH₂CO₂Me), 2.99 (m, 1H, —CH₂N—), 2.70 (m, 2H, ArCH₂CH₂CO₂Me), 2.41 (c, 1H, J=8.6 Hz, —CH₂N—), 2.69-1.85 (m, 4H, —CH₂—CH₂—), 1.71-1.55 (m, 9H, NHCH₂—CH₂—), 1.36 (m, 2H, —CH₂—CH₂—), 1.25-1.19 (m, 6H, —CH₂—CH₂—).

Example 10d

3-(6-{2R-[4-(4-Cyclohexyl-butylcarbamoyl)-oxazol-2-yl]-pyrrolidin-1-ylmethyl}-benzo[1,3]dioxol-5-yl)-propionic acid methyl ester $^1$H-NMR (CDCl$_3$, 300 MHz): 8.18 (d, 1H, J=15.9 Hz, —CH=CH—CO$_2$Me), 8.16 (s, 1H, =CH), 7.28 (m, 1H, NH), 7.04 (s, 1H, ArH), 6.76 (s, 1H, ArH), 6.21 (d, 1H, J=15.9 Hz, —CH=CH—CO$_2$Me), 5.96 (s, 2H, —OCH$_2$O—), 3.96 (d, 1H, J=11.9 Hz, —NCH$_2$Ar), 3.72 (t, 1H, J=7.7 Hz, NCH-Oxazole), 3.43 (d, 1H, J=11.9 Hz, —NCH$_2$Ar), 3.40 (dd, 2H, J=7, 14 Hz, CONHCH$_2$—), 2.96 (m, 1H, —CH$_2$N—), 2.85 (m, 2H, ArCH$_2$CH$_2$CO$_2$Me), 2.69 (m, 2H, ArCH$_2$CH$_2$CO$_2$Me), 2.37 (c, 1H, J=8.6 Hz, —CH$_2$N—), 2.69-1.85 (m, 4H, —CH$_2$—CH$_2$—), 1.71-1.55 (m, 9H, NHCH$_2$—CH$_2$—), 1.36 (m, 2H, —CH$_2$—CH$_2$—), 1.25-1.19 (m, 6H, —CH$_2$—CH$_2$—).

Example 10e 3-(2-{2R-[4-(octylcarbamoyl)-oxazol-2-yl]-pyrrolidin-1-ylmethyl}-4-fluoro-phenyl)-propionic acid methyl ester $^1$H-NMR (CDCl$_3$, 300 MHz): 8.09 (s, 1H, =CH), 7.08 (dd, 1H, J=5.5, 8.4 Hz, ArH), 7.01 (m, 1H, NH), 6.98 (dd, 1H, J=2.6, 9.5 Hz, ArH), 6.97 (dt, 1H, J=2.6, 8.4, ArH), 3.88 (d, 1H, J=11.9 Hz, —NCH$_2$Ar), 3.76 (t, 1H, J=7.7 Hz, NCH-Oxazole), 3.68 (s, 3H, —CO$_2$CH$_3$), 3.42 (d, 1H, J=11.9 Hz, —NCH$_2$Ar), 3.41 (dd, 2H, J=7, 14 Hz, CONHCH$_2$—), 3.10 (m, 2H, ArCH$_2$CH$_2$CO$_2$Me), 3.00 (m, 2H, —CH$_2$N—), 2.70 (m, 2H, ArCH$_2$CH$_2$CO$_2$Me), 2.69-1.85 (m, 4H, —CH$_2$—CH$_2$—), 1.71-1.55 (m, 2H, NHCH$_2$—CH$_2$—), 1.25-1.19 (m, 8H, —CH$_2$—CH$_2$—), 0.89 (m, 3H, —CH$_3$).
$^{19}$F-NMR(CDCl$_3$, 300 MHz) δ –111

Example 11

General method 11

The ester (from general method 10) (1.82 mmol) was dissolved in THF (20 mL) and a solution of LiOH (0.302 g, 7.3 mmol) in water (10 mL) was added. The resulting mixture was heated at 60° C. for 16 h.

Then, EtOAc was added (10 ml) and the solution was neutralized with a 2M solution of HCl. The organic layer was separated, washed with brine (10 mL) and dried (Na$_2$SO$_4$). The mixture was filtered and the solvent was evaporated to give crude product.

The compound was purified by column chromatography on a 10 g SPE cartridge, using as eluent: 2% MeOH/98% CH$_2$Cl$_2$, to give the carboxylic acid as a white solid (70%).

Example 11a

3-(2-{2R-[4-(4-Cyclohexyl-butylcarbamoyl)-oxazol-2-yl]-pyrrolidin-1-ylmethyl}-4-fluoro-phenyl)-propionic acid $^1$H-NMR (CDCl$_3$, 300 MHz): 8.18 (s, 1H, =CH), 7.10 (m, 2H, ArH+NH), 6.97 (m, 1H, ArH), 6.88 (m, 1H, ArH), 3.90 (d, 1H, J=11.9 Hz, —NCH$_2$Ar), 3.77 (t, 1H, J=7.7 Hz, NCH-Oxazole), 3.40 (m, 3H, —NCH$_2$Ar+CONHCH$_2$—), 2.99 (m, 1H, —CH$_2$N—), 2.88 (m, 2H, ArCH$_2$CH$_2$CO$_2$H), 2.59 (m, 2H, ArCH$_2$CH$_2$CO$_2$H), 2.41 (m, 1H, —CH$_2$N—), 2.24-1.90 (m, 4H, —CH$_2$—CH$_2$—), 1.60 (m, 2H, NHCH$_2$—CH$_2$—), 1.27 (m, 10H, —CH$_2$—CH$_2$—), 0.88 (m, 5H, —CH$_2$—CH$_2$—). $^{19}$F-NMR(CDCl$_3$, 300 MHz) δ –111

Example 11b

3-(2-{2R-[4-(4-Cyclohexyl-butylcarbamoyl)-oxazol-2-yl]-pyrrolidin-1-ylmethyl}-4-chloro-phenyl)-propionic acid $^1$H-NMR (CDCl$_3$, 300 MHz): 8.16 (s, 1H, =CH), 7.19 (m, 2H, ArH), 7.09 (d, 1H, J=8.4 Hz, ArH), 7.02 (m, 1H, NH), 3.91 (d, 1H, J=11.9 Hz, —NCH$_2$Ar), 3.76 (t, 1H, J=7.7 Hz, NCH-Oxazole), 3.40 (m, 3H, —NCH$_2$Ar+CONHCH$_2$—), 3.00 (m, 1H, —CH$_2$N—), 2.87 (m, 2H, ArCH$_2$CH$_2$CO$_2$H), 2.60 (m, 2H, ArCH$_2$CH$_2$CO$_2$H), 2.41 (m, 1H, —CH$_2$N—), 2.24-1.90 (m, 4H, —CH$_2$—CH$_2$—), 1.60 (m, 2H, NHCH$_2$—CH$_2$—), 1.27 (m, 10H, —CH$_2$—CH$_2$—), 0.88 (m, 5H, —CH$_2$—CH$_2$—).

Example 11c

3-(2-{2R-[4-(4-Cyclohexyl-butylcarbamoyl)-oxazol-2-yl]-pyrrolidin-1-ylmethyl}-4-methoxy-phenyl)-propionic acid $^1$H-NMR (CDCl$_3$, 300 MHz): 8.18 (s, 1H, =CH), 7.07 (m, 2H, ArH+NH), 6.77 (m, 2H, ArH), 3.91 (d, 1H, J=11.9 Hz, —NCH$_2$Ar), 3.77 (s, 3H, ArOCH$_3$), 3.77 (t, 1H, J=7.7 Hz, NCH-Oxazole), 3.38 (m, 3H, —NCH$_2$Ar+CONHCH$_2$—), 3.00 (m, 1H, —CH$_2$N—), 2.85 (m, 2H, ArCH$_2$CH$_2$CO$_2$H), 2.59 (m, 2H, ArCH$_2$CH$_2$CO$_2$H), 2.41 (m, 1H, —CH$_2$N—), 2.24-1.90 (m, 4H, —CH$_2$—CH$_2$—), 1.60 (m, 2H, NHCH$_2$—CH$_2$—), 1.27 (m, 10H, —CH$_2$—CH$_2$—), 0.88 (m, 5H, —CH$_2$—CH$_2$—).

Example 11c

3-(6-{2R-[4-(4-Cyclohexyl-butylcarbamoyl)-oxazol-2-yl]-pyrrolidin-1-ylmethyl}-benzo[1,3]dioxol-5-yl)-propionic acid $^1$H-NMR (CDCl$_3$, 300 MHz): 8.19 (s, 1H, =CH), 7.11 (m, 1H, NH), 6.69 (s, 1H, ArH), 6.64 (s, 1H, ArH), 5.89 (s, 2H, —OCH$_2$O—), 3.84 (d, 1H, J=11.9 Hz, —NCH$_2$Ar), 3.72 (t, 1H, J=7.7 Hz, NCH-Oxazole), 3.39 (dd, 2H, J=7, 14 Hz, CONHCH$_2$—), 3.29 (d, 1H, J=11.9 Hz, —NCH$_2$Ar), 3.00 (m, 1H, —CH$_2$N—), 2.79 (m, 2H, ArCH$_2$CH$_2$CO$_2$H), 2.60 (m, 2H, ArCH$_2$CH$_2$CO$_2$H), 2.38 (c, 1H, J=8.6 Hz, —CH$_2$N—), 2.69-1.85 (m, 4H, —CH$_2$—CH$_2$—), 1.71-1.55 (m, 9H, NHCH$_2$—CH$_2$—), 1.36 (m, 2H, —CH$_2$—CH$_2$—), 1.25-1.19 (m, 6H, —CH$_2$—CH$_2$—).

Example 11d 3-(2-{2R-[4-(octylcarbamoyl)-oxazol-2-yl]-pyrrolidin-1-ylmethyl}-4-fluoro-phenyl)-propionic acid $^1$H-NMR (CDCl$_3$, 300 MHz): 8.16 (s, 1H, =CH), 7.09 (m, 2H, ArH+NH), 6.95 (dd, 1H, J=2.6, 9.5 Hz, ArH), 6.82 (dt, 1H, J=2.6, 8.4 Hz, ArH), 3.85 (d, 1H, J=11.9 Hz, —NCH$_2$Ar), 3.73 (t, 1H, J=7.7 Hz, NCH-Oxazole), 3.36 (m, 3H, —NCH$_2$Ar+CONHCH$_2$—), 2.86 (m, 3H, ArCH$_2$CH$_2$CO$_2$Me+—CH$_2$N—), 2.60 (m, 2H, ArCH$_2$CH$_2$CO$_2$Me), 2.36 (m, 1H, —CH$_2$N), 2.24-1.80 (m, 4H, —CH$_2$—CH$_2$—), 1.71-1.55 (m, 4H, NHCH$_2$—CH$_2$—), 1.25-1.19 (m, 8H, —CH$_2$—CH$_2$—), 0.89 (m, 3H, —CH$_3$).

$^{19}$F-NMR(CDCl$_3$, 300 MHz) δ −111

Example 12

General Method 12

To a solution of saturated acid (from general method 11) (0.15 mmol) in THF (7 mL), under nitrogen atmosphere, was added pyridine (0.45 mmol) and cyanuric fluoride (1.125 mmol) and the resulting mixture was refluxed for 4 h. The reaction mixture was left to cool to room temperature, then diluted with ethyl acetate (15 mL) and water (10 mL). The organic layer was separated, washed with a saturated solution of NaHCO$_3$ (10 mL), then saturated brine (10 mL), dried (MgSO$_4$), filtered and the solvent was evaporated under vacuum.

The crude was re-dissolved in CH$_2$Cl$_2$ (7 mL) and DMAP (0.6 mmol) and trifluromethanesulfonamide (0.45 mmol) were added. The resulting mixture was stirred at room temperature under nitrogen for 16 h.

After this time, the reaction mixture was diluted with more CH$_2$Cl$_2$ (15 mL) and water (10 mL) was added. The organic layer was separated, washed with a 2M solution of HCl (5 mL), then saturated brine (10 mL) and dried (MgSO$_4$), filtered and the solvent was evaporated under vacuum.

The residue was purified by column chromatography through a 10 g SPE silica cartridge using a solvent gradient starting from ethyl acetate to ethyl acetate/methanol 9:1, to isolate the title compound as thick oil (60%).

Example 12a

S)—N-(4-cyclohexylbutyl)-2-(1-(5-fluoro-2-(3-oxo-3-(trifluoromethylsulfonamido) propyl)benzyl)pyrrolidin-2-yl)oxazole-4-carboxamide $^1$H-NMR (CDCl$_3$, 300 MHz): 8.27 (s, 1H, =CH), 7.24 (m, 1H, NH), 7.05 (dd, 1H, J=6, 8.4 Hz, ArH), 6.85 (m, 2H, ArH), 3.91 (d, 1H, J=11.9 Hz, —NCH$_2$Ar), 3.74 (t, 1H, J=7.7 Hz, NCH-Oxazole), 3.36 (m, 2H, CONHCH$_2$—), 3.23 (d, 1H, —NCH$_2$Ar), 2.99 (m, 1H, —CH$_2$N—), 2.59 (m, 4H, ArCH$_2$CH$_2$CO$_2$H), 2.49 (m, 1H, —CH$_2$N—), 2.40-2.20 (m, 4H, —CH$_2$—CH$_2$—), 1.90 (m, 2H, NHCH$_2$—CH$_2$—), 1.27 (m, 10H, —CH$_2$—CH$_2$—), 0.88 (m, 5H, —CH$_2$—CH$_2$—).
$^{19}$F-NMR(CDCl$_3$, 300 MHz) δ −79, −118
LC-MS (M$^+$+1) 631

Example 12b

(S)—N-(4-cyclohexylbutyl)-2-(1-(5-chloro-2-(3-oxo-3-(trifluoromethylsulfonamido) propyl)benzyl)pyrrolidin-2-yl)oxazole-4-carboxamide $^1$H-NMR (CDCl$_3$, 300 MHz): 8.33 (s, 1H, =CH), 7.15 (m, 2H, ArH), 7.04 (m, 1H, ArH), 7.02 (m, 1H, NH), 4.01 (m, 2H, —NCH$_2$Ar+NCH-Oxazole), 3.39 (m, 3H, CONHCH$_2$—+—NCH$_2$Ar), 3.15 (m, 1H, —CH$_2$N—), 2.70-2.46 (m, 5H, ArCH$_2$CH$_2$CONH+—CH$_2$N—), 2.29 (m, 2H, —CH$_2$—CH$_2$—), 2.03 (m, 2H, —CH$_2$—CH$_2$—), 1.90 (m, 2H, NHCH$_2$—CH$_2$—), 1.27 (m, 10H, —CH$_2$—CH$_2$—), 0.88 (m, 5H, —CH$_2$—CH$_2$—). $^{19}$F-NMR(CDCl$_3$, 300 MHz) −79
LC-MS (M$^+$+1) 647

Example 12c (S)—N-(4-cyclohexylbutyl)-2-(1-(5-methoxy-2-(3-oxo-3-(trifluoromethyl sulfonamido)propyl)benzyl)pyrrolidin-2-yl)oxazole-4-carboxamide

$^1$H-NMR (CDCl$_3$, 300 MHz): 8.23 (s, 1H, =CH), 7.06 (m, 2H, ArH), 6.75 (m, 2H, ArH+NH), 3.95 (d, 1H, J=11.9 Hz, —NCH$_2$Ar), 3.77 (m, 4H, NCHOxazole+ArOCH$_3$), 3.41 (m, 2H, CONHCH$_2$), 3.25 (d, 1H, J=11.9 Hz, —NCH$_2$Ar), 3.01 (m, 1H, —CH$_2$N—), 2.71 (m, 3H, ArCH$_2$CH$_2$CO$_2$H), 2.71 (m, 3H, ArCH$_2$CH$_2$CO$_2$H), 2.51 (m, 1H, ArCH$_2$CH$_2$CO$_2$H), 2.41 (m, 1H, —CH$_2$N—), 2.21 (m, 2H, —CH$_2$—CH$_2$—), 1.97 (m, 2H, —CH$_2$—CH$_2$—), 1.90 (m, 2H, NHCH$_2$—CH$_2$—), 1.27 (m, 10H, —CH$_2$—CH$_2$—), 0.88 (m, 5H, —CH$_2$—CH$_2$—). $^{19}$F-NMR(CDCl$_3$, 300 MHz) δ −79

LC-MS (M$^+$+1) 643

Example 12d

N-(4-cyclohexylbutyl)-2-(1-{[6-(3-oxo{[(trifluoromethylsulfonamido)propyl)-1,3-benzodioxol-5-yl]methyl}pyrrolidin-2-yl)-1,3-oxazole-4-carboxamide

$^1$H-NMR (CDCl$_3$, 300 MHz): 8.34 (s, 1H, =CH), 7.32 (m, 1H, NH), 6.62 (s, 1H, ArH), 6.60 (s, 1H, ArH), 5.88 (s, 2H, —OCH$_2$O—), 3.86 (d, 1H, J=11.9 Hz, —NCH$_2$Ar), 3.74 (t, 1H, J=7.7 Hz, NCH-Oxazole), 3.41 (m, 3H, CONHCH$_2$—+—NCH$_2$Ar), 3.05 (m, 1H, —CH$_2$N—), 2.38 (m, 4H, ArCH$_2$CH$_2$CO$_2$H), 2.00 (c, 1H, J=8.6 Hz, —CH$_2$N—), 2.69-1.85 (m, 4H, —CH$_2$—CH$_2$—), 1.71-1.55 (m, 9H, NHCH$_2$—CH$_2$—), 1.36 (m, 2H, —CH$_2$—CH$_2$—), 1.25-1.19 (m, 6H, —CH$_2$—CH$_2$—).

$^{19}$F-NMR(CDCl$_3$, 300 MHz) δ −79.7

LC-MS (M$^+$+1) 657

Example 12e

2-{1-[5-fluoro-2-(3-oxo-3-{[(trifluoromethyl)sulfonyl]amino}propyl)benzyl]pyrrolidin-2-yl}-N-octyl-1,3-oxazole-4-carboxamide $^1$H-NMR (CDCl$_3$, 300 MHz): 8.38 (s, 1H, =CH), 7.09 (m, 1H, NH), 7.01 (m, 1H, ArH), 6.84 (m, 2H, ArH), 3.92 (d, 1H, J=11.9 Hz, —NCH$_2$Ar), 3.76 (t, 1H, J=7.7 Hz, NCH-Oxazole), 3.36 (m, 2H, CONHCH$_2$—), 3.17 (d, 1H, J=11.9 Hz, —NCH$_2$Ar), 2.98 (m, 1H, —CH$_2$N—), 2.63- 2.30 (m, 5H, ArCH$_2$CH$_2$CO$_2$Me+—CH$_2$—CH$_2$-+—CH$_2$N—), 2.19 (m, 2H, ArCH$_2$CH$_2$CO$_2$Me), 1.92 (m, 2H, —CH$_2$—CH$_2$—), 1.25-1.19 (m, 12H, —CH$_2$—CH$_2$—), 0.89 (m, 3H, —CH$_3$).

$^{19}$F-NMR(CDCl$_3$, 300 MHz) δ −79.7, −118.5

LC-MS (M$^+$+1) 605

The above compounds were tested for PG antagonist activity as follows using human recombinant prostanoid receptor (DP$_1$, EP$_{1-4}$, FP, IP and TP) stable cell lines.

In order to measure the response of G$_s$ and G$_i$ coupled prostanoid receptors as a Ca$^{2+}$ signal, chimeric G protein cDNAs were used. Stable cell lines over-expressing human prostanoid DP$_1$, EP$_{1-4}$, FP, IP, and TP receptors were established as follows:

Briefly, human prostanoid DP$_1$, EP$_2$, and EP$_4$ receptor cDNAs were co-transfected with chimeric G$_{qs}$ cDNA containing a haemagglutanin (HA) epitope; human prostanoid EP$_3$ receptors were co-transfected with chimeric G$_{qi}$-HA; human EP$_1$, FP, IP, and TP receptor cDNAs were expressed with no exogenous G-proteins. G$_{qs}$ and G$_{qi}$ chimeric cDNAs (Molecular Devices, Sunnyvale, Calif., U.S.A.), as well as cDNAs of prostanoid receptors, were cloned into a pCEP$_4$ vector with a hygromycin B selection marker. Transfection into HEK-293 EBNA (Epstein-Barr virus nuclear antigen) cells was achieved by the FuGENE 6 transfection Reagent (Roche Applied Science, Indianapolis, Ind., USA). Stable transfectants were selected according to hygromycin resistance. Because G$_{qs}$ and G$_{qi}$ contained an HA epitope, G-protein expression was detected by Western blotting analysis using anti-mouse HA monoclonal antibody and horseradish peroxidase (HRP)-conjugated secondary antibody, while functional expression of prostanoid receptors was detected by FLIPR screening. These stable cell lines were validated using previously published antagonists at 10 μM against serial dilutions of standard agonists by FLIPR functional assays for Ca$^{2+}$ Signaling (as described below).

Ca$^{2+}$ signaling studies were performed using a FLIPR TETRA system (Molecular Devices, Sunnyvale, Calif., USA) in the 384-format. This is a high-throughput instrument for cell-based assays to monitor Ca$^{2+}$ signaling associated with GPCRs and ion channels. Cells were seeded at a density of 5×10$^4$ cells/well in BioCoat poly-D-lysine coated, black wall, clear bottom 384-well plates (BD Biosciences, Franklin lakes, NJ, USA) and allowed to attach overnight in an incubator at 37° C. The cells were then washed twice with HBSS-HEPES buffer (Hanks' balanced salt solution without bicarbonate and phenol red, 20 mM HEPES, pH 7.4) using an ELx405 Select CW Microplate Washer (BioTek, Winooski, Vt., USA). After 60 min of dye-loading in the dark using the Ca$^{2+}$-sensitive dye Fluo-4AM (Invitrogen, Carlsbad, Calif., USA), at a final concentration of 2×10$^{-6}$M, the plates were washed 4 times with HBSS-HEPES buffer to remove excess dye and leaving 50 μl of buffer in each well. The plates were then placed in the FLIPR TETRA instrument and allowed to equilibrate at 37° C. AGN-211377 was added in a 25 μl volume to each well to give final concentrations of 0.1 μM, 0.3 μM, 1 μM, 3 μM, 10 μM, and 30 μM; or 0.067 μM, 0.1 μM, 0.2 μM, 0.3 μM, 0.67 μM, and 1 μM for cells over-expressing TP receptors.

After 4.5 minutes, a 7-point serial dilution of the standard agonist for the corresponding receptor, in a 25 μl volume was injected at the final concentrations from 10$^{-11}$M to 10$^{-5}$M in 10-fold serial dilution increments for cells expressing human recombinant DP$_1$, EP$_1$, EP$_2$, EP$_3$, EP$_4$, FP, and IP receptors. The dose range for the standard agonist for human recombinant TP receptors was from 10$^{-12}$M to 10$^{-6}$M. HBSS-HEPES buffer was used as the negative control for the standard agonists. Cells were excited with LED (light emitting diode) excitation at 470-495 nm and emission was measured through an emission filter at 515-575 nm. Assay plates were read for 3.5 minutes using the FLIPR$^{TETRA}$. The peak increase in fluorescence intensity was recorded for each well. On each plate, negative controls, dose response of positive controls, and co-treatments of antagonist-agonist for each dose were in triplicates. Standard agonists were as follows: DP=BW 245C, $EP_1$-$EP_4$=$PGE_2$, FP=17-phenyl-$PGF_{2\alpha}$, IP=Cicaprost, and TP=U-46619. The peak fluorescence change in each well containing drug was expressed relative to vehicle controls with the standard agonist at $10^{-6}$M (the positive control). To obtain concentration-response curves, compounds were tested in triplicate in each plate over the desired concentration range.

$Ca^{2+}$ Signal Studies on Human Recombinant Prostanoid Receptor $DP_2$

FLIPR functional assays were conducted to monitor the activity anti-asthmatic against human $DP_2$ receptors stably expressed in the Chem-5 proprietary host cell line generated by Millipore. Prior to standard agonist addition, the compounds were spotted at 10 µM along with vehicle control (1% Ethanol in HBSS-HEPES buffer) across the assay wells. The assay plate was incubated at room temperature for 10 minutes in the dark. Then an 8-point serial dilution dose response from $10^{-12}$M to $10^{-5}$M of the standard agonist $PGD_2$ was performed. Assay plates were read for 90 seconds using the FLIPR$^{TETRA}$. The fluorescence measurements were collected to calculate $IC_{50}$ values. The assays were done at least 3 times to give n=3.

All plates were subjected to appropriate baseline corrections. Maximum fluorescence values were exported. The raw data of n=1 was first processed by Activity Base using nonlinear regression curve fit to calculate the percentage activity of each data point relative to the positive control (=$10^{-6}$M of the standard agonist). Then n=3 of this data were exported to GraphPad Prism 4 to calculate the average $EC_{50}$ of the standard agonist, and the $IC_{50}$ (the concentration of the antagonist required to inhibit half the standard agonist activity) were calculated using nonlinear regression curve fit, with constraints of bottom constant equal to 0 and top constant equal to 100. Calculation of Kb=[Antagonist Concentration]/($IC_{50}/EC_{50}$−1). When no antagonism was detected or when Kb≥10,000 nM, the antagonist is defined as not active (NA).

The results of the above testing are reported in TABLE 1, below.

TABLE 1

EC50 (nM) on Prostanoid Receptor Functional Activity Measured by FLIPR

| Example No | FP | DP | EP1 | EP2 | EP3 | EP4 | IP | TP |
|---|---|---|---|---|---|---|---|---|
| 12a | 350 | <1 | 47 | 6400 | 82 | 38 | 550 | <1 |
|  | 270 | 17 | 20 | 830 | 47 | 10 | 860 | <1 |
| 12b | 460 | <1 | 70 | 5500 | 100 | 37 | 9500 | <1 |
| 12d | 360 | 3 | 63 | 3900 | 150 | 7 | 1000 | 0.3 |
| 12e | 270 | 18 | 20 | 2500 | 110 | 19 | 290 | >1 |

(FLIPR) $K_b$ (nM), NA = inactive

As shown in TABLE 1, the preferred compounds of this invention are pan antagonists having particular activity at the FP, DP, $EP_1$, $EP_3$, $EP_4$ and TP receptors, but are much less active at the $EP_2$ and IP receptors. Thus, these compounds have a biological selectivity profile making them useful in treating diseases and conditions which are mediated by the FP, DP, $EP_1$, $EP_3$, $EP_4$ and TP receptors, without the potential side effects and biological limitations associated with IP and $EP_2$ receptor blockade. Thus, the compounds of this invention compound may be administered to treat $DP_1$, FP, $EP_1$, $EP_3$, TP and/or $EP_4$ receptor mediated diseases or conditions.

For example, said condition or disease may be related to inflammation, or said $DP_1$, FP, $EP_1$, $EP_3$, TP and/or $EP_4$ receptor mediated condition or disease may be selected from the group consisting of allergic conditions, asthma, allergic asthma, apnea, allergic conjunctivitis, allergic rhinitis, atopic dermatitis, uveitis and related disorders, atherosclerosis, blood coagulation disorders, bone disorders, cancer, cellular neoplastic transformations, chronic obstructive pulmonary diseases and other forms of lung inflammation, pneumonia, congestive heart failure, diabetic retinopathy, diseases or conditions requiring a treatment of anti-coagulation, diseases requiring control of bone formation and resorption, fertility disorders, pre-term labor, endometriosis glaucoma, hyperpyrexia, immune and autoimmune diseases, inflammatory conditions, metastic tumor growth, migraine, mucus secretion disorders, nasal congestion, nasal inflammation, occlusive vascular diseases, ocular hypertension, ocular hypotension, osteoporosis, rheumatoid arthritis, pain, perennial rhinitis, pulmonary congestion, pulmonary hypotension, Raynaud's disease, rejection in organ transplant and by-pass surgery, respiratory conditions, hirsutism, rhinorrhea, shock, sleep disorders, and sleep-wake cycle disorders, over active bladder disorders.

Said compound may be administered as a surgical adjunct in ophthalmology for cataract removal and artificial lens insertion, ocular implant procedures, photorefractive radial keratotomy and other ophthalmogical laser procedures or as a surgical adjunct in a procedure involving skin incisions, relief of pain and inflammation and scar formation/keloids post-surgery, for treating sports injuries and general aches and pains in muscles and joints. Preferably, said $DP_1$, FP, $EP_1$, EP3, TP, and/or $EP_4$ receptor mediated condition or disease is an $EP_1$ and/or $EP_4$ receptor mediated condition or disease.

Preferably, said $DP_1$, FP, $EP_1$, $EP_3$, TP and/or $EP_4$ receptor mediated condition or disease is an allergic condition, e.g. an dermatological allergy, or an ocular allergy, or a respiratory allergy, e.g. nasal congestion, rhinitis, and asthma.

Said condition or disease may be related to pain.

Said condition or disease may be selected from the group consisting of arthritis, migraine, and headache.

Said condition or disease may be associated with the gastrointestinal tract, wherein said condition or disease may be peptic ulcer, heartburn, reflux esophagitis, erosive esophagitis, non-ulcer dyspepsia, infection by *Helicobacter pylori*, alrynitis, and irritable bowel syndrome.

Said condition or disease may be selected from the group consisting of hyperalgesia and allodynia, or said condition or disease may be related to mucus secretion, wherein said mucus secretion is gastrointestinal, or occurs in the nose, sinuses, throat, or lungs.

Said condition or disease is related to abdominal cramping, e.g. said condition or disease may be irritable bowel syndrome.

Said condition or disease may be a bleeding disorder, or a sleep disorder, or mastocytosis.

Said condition or disease may be associated with elevated body temperature, or ocular hypertension and glaucoma, or ocular hypotension.

Said condition may relate to surgical procedures to treat pain, inflammation and other unwanted sequelae wherein said surgical procedure includes incision, laser surgery or implantation.

Finally, said condition may be related to pain and inflammation and post-surgical scar and keloid formation.

In view of the various diseases and conditions that may be treated with the compositions of this invention there is provided a pharmaceutical product comprising a compound having the following formula wherein $R_1$ is selected from the group consisting of $CO_2R_7$ and
$CON(R_7)SO_2R_7$ wherein $R_7$ is selected from the group consisting of H, alkyl and aryl, wherein said alkyl and aryl may be substituted with halo or haloalkyl, e.g. fluoro or fluoroalkyl;
$R_2$ is selected from the group consisting of H, alkyl, halogen, $OR_7$ and $OC(R_7)_2O$; and
$R_3$ is selected from the group consisting of H and alkyl; or a pharmaceutically acceptable salt or a prodrug thereof, wherein said product is packaged and labeled for the treatment or prevention of a disease or condition selected from the group consisting of uveitis, allergic conditions, asthma, allergic asthma, allergic rhinitis, atherosclerosis, blood coagulation disorders, bone disorders, cancer, cellular neoplastic transformations, chronic obstructive pulmonary diseases and other forms of lung inflammation, congestive heart failure, diabetic retinopathy, diseases or conditions requiring a treatment of anti-coagulation, diseases requiring control of bone formation and resorption, fertility disorders, hyperpyrexia, gangrene, glaucoma, hypothermia, immune and autoimmune diseases, inflammatory conditions, metastic tumor growth, migraine, mucus secretion disorders, nasal congestion, nasal inflammation, occlusive vascular diseases, ocular hypertension, ocular hypotension, osteoporosis, pain, perennial rhinitis, pulmonary congestion, pulmonary hypotension, Raynaud's disease, rejection in organ transplant and by-pass surgery, respiratory conditions, rheumatoid arthritis, rhinorrhea, shock, sleep disorders, sleep-wake cycle disorders, sports injuries, muscle aches and pains, and surgical adjunct for minimizing pain, inflammation and scar/keloid formation.

Those skilled in the art will readily understand that for administration the compounds disclosed herein can be admixed with pharmaceutically acceptable excipients which, per se, are well known in the art. Specifically, a drug to be administered systemically, it may be formulated as a powder, pill, tablet or the like, or as a solution, emulsion, suspension, aerosol, syrup or elixir suitable for oral or parenteral administration or inhalation.

For solid dosage forms, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distcarate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the compounds of the present invention and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectable formulations can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds of the present invention administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds is preferably in the range of about 0.5 ng/kg/day to of about 250 mg/kg/day or about 1 ng/kg/day to about 100 mg/kg/day.

For ophthalmic application, solutions are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

Similarly, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

For topical use, creams, ointments, gels, solutions or suspensions, etc., containing the compound of the present invention are employed. Topical formulations may generally be comprised of a pharmaceutical carrier, cosolvent, emulsifier, penetration enhancer, preservative system, and emollient.

The actual dose of the compounds of the present invention depends on the specific compound, and on the condition to be treated; the selection of the appropriate dose is well within the knowledge of the skilled artisan.

The present invention is not to be limited in scope by the exemplified embodiments, which are only intended as illustrations of specific aspects of the invention. Various modifications of the invention, in addition to those disclosed herein, will be apparent to those skilled in the art by a careful reading of the specification, including the claims, as originally filed. In particular, while the present invention has been illustrated by the N-alkyl-2-(1-(5-substituted-2-(3-oxo-3-(trifluoromethylsulfonamido)propyl)benzyl)pyrrolidin-2-yl)oxazole-4-carboxamide compounds disclosed herein, the corresponding, 3-(2-{2R-[4-(4-alkylcarbamoyl)-oxazol-2-yl]-pyrrolidin-1-ylmethyl}-4-substituted-phenyl)-propionic acid alkyl esters and the corresponding 3-(2-{2R-[4-(4-alkylcarbamoyl)-oxazol-2-yl]-pyrrolidin-1-ylmethyl}-4-substituted-phenyl)-propionic acids, e.g. the compounds of the above general formula, as well as the unsubstituted derivatives thereof, may be used in the practice of the method of this invention.

It is intended that all such modifications will fall within the scope of the appended method of treatment claims and the package claims hereof.

What is claimed is:

1. A compound having the following formula:

wherein $R_1$ is selected from the group consisting of $CO_2R_7$ wherein $R_7$ is selected from the group consisting of H, alkyl and aryl, wherein said alkyl and aryl may be substituted with halo or haloalkyl, $R_2$ is selected from the group consisting of alkyl, halogen, and $OR_7$; and $R_3$ is selected from the group consisting of H alkyl, and cycloalkyl-substituted alkyl.

2. The compound of claim 1 wherein $R_2$ is selected from the group consisting of F, Cl, and $OCH_3$.

3. The compound of claim 1 wherein $R_3$ is alkyl.

4. The compound of claim 1 wherein, $R_3$ is $(CH_2)_nCH_2R_8$, wherein n is an integer of from 4 to 9 and $R_8$ is H or cyclohexyl.

5. The compound of claim 1 wherein, $R_7$ is selected from the group consisting of methyl, ethyl, i-propyl, trifluoromethyl and cyclopropyl.

6. The compound of claim 1, wherein said compound is selected from the group consisting of:

3-(2-{2R-[4-(4-Cyclohexyl-butylcarbamoyl)-oxazol-2-yl]-pyrrolidin-1-ylmethyl}-4-fluoro-phenyl)-propionic acid methyl ester;

3-(2-{2R[4-(4-Cyclohexyl-butylcarbamoyl)-oxazol-2-yl]-pyrrolidin-1-ylmethyl}-4-chloro-phenyl)-propionic acid methyl ester;

3-(2-{2R-[4-(4-Cyclohexyl-butylcarbamoyl)-oxazol-2-yl]-pyrrolidin-1-ylmethyl}-4-methoxy-phenyl)-propionic acid methyl ester;

3-(2-{2R-[4-(octylcarbamoyl)-oxazol-2-yl]-pyrrolidin-1-ylmethyl}-4-fluoro-phenyl)-propionic acid methyl ester;

3-(2-{2R-[4-(4-Cyclohexyl-butylcarbamoyl)-oxazol-2-yl]-pyrrolidin-1-ylmethyl}-4-fluoro-phenyl)-propionic acid;

3-(2-{2R[4-(4-Cyclohexyl-butylcarbamoyl)-oxazol-2-yl]-pyrrolidin-1-ylmethyl}-4-chloro-phenyl)-propionic acid;

3-(2-{2R[4-(4-Cyclohexyl-butylcarbamoyl)-oxazol-2-yl]-pyrrolidin-1-ylmethyl}-4-methoxy-phenyl)-propionic acid; and 3-(2-{2R-[4-(octylcarbamoyl)-oxazol-2-yl]-pyrrolidin-1-ylmethyl}-4-fluoro-phenyl)-propionic acid.

7. A method comprising administering a compound of claim 1 to treat DP1, FP, EP1, EP3, TP and/or EP4 receptor mediated diseases or conditions selected from the group consisting of allergic conditions, asthma, allergic asthma, allergic conjunctivitis, allergic rhinitis, atopic dermatitis, uveitis, atherosclerosis, chronic obstructive pulmonary diseases, pneumonia-, congestive heart failure, diabetic retinopathy, diseases or conditions requiring a treatment of anti-coagulation, endometriosis, glaucoma, hyperpyrexia, inflammatory conditions, migraine, nasal congestion, nasal inflammation, ocular hypertension, osteoporosis, rheumatoid arthritis, pain, pulmonary congestion, and pulmonary hypotension.

* * * * *